United States Patent [19]

Friauf et al.

[11] 4,415,807
[45] Nov. 15, 1983

[54] CROSS-SLICE DATA ACQUISITION SYSTEM FOR PET SCANNER

[75] Inventors: Walter S. Friauf; Rodney A. Brooks, both of Bethesda; Horace E. Cascio, Olney; Victor Sank, Rockville, all of Md.

[73] Assignee: The United States of America as represented by the Department of Health and Human Services, Washington, D.C.

[21] Appl. No.: 250,840

[22] Filed: Apr. 3, 1981

[51] Int. Cl.$^3$ .............................................. G01T 1/20
[52] U.S. Cl. ................................ 250/363 S; 250/369
[58] Field of Search ................ 250/363 R, 363 S, 366, 250/369

[56] References Cited

U.S. PATENT DOCUMENTS

| | | | |
|---|---|---|---|
| 4,057,727 | 11/1977 | Muehllehner et al. | 250/363 S |
| 4,150,292 | 4/1979 | Ter-Pogossian | 250/363 S |
| 4,216,526 | 8/1980 | Karwowski | 364/414 |
| 4,217,609 | 8/1980 | Hatori et al. | 358/136 |
| 4,284,890 | 8/1981 | Thompson | 250/363 S |

OTHER PUBLICATIONS

Brooks et al. "Design of a High Resolution Positron Emission Tomograph: The Neuro-PET," J. Comput Assist. Tomogr., vol. 4, No. 1, 1980, pp. 5-13.

Primary Examiner—Janice A. Howell
Attorney, Agent, or Firm—Holman & Stern

[57] ABSTRACT

A positron emission tomographic scanner is provided with cross-slice event data handling capability by adding only a coincidence detector and register in common to the circuitry for two adjacent planar detector arrays and adding an OR gate to the circuitry for each array. The improvement permits the same circuitry to be utilized for both cross-slice event processing and intra-slice event processing. Selection of the identification code for a detector is determined by a first coincidence detector in the case of an intra-slice event and the added coincidence detector in the case of an inter-slice event.

7 Claims, 2 Drawing Figures

CROSS-SLICE DATA ACQUISITION SYSTEM FOR PET SCANNER

TECHNICAL FIELD

The present invention relates to computed tomography systems and more particularly to diagnostic positron emission tomography (PET) scanners.

BACKGROUND OF THE INVENTION

Diagnostic utilization of positron emission tomography involves administering a radionuclide to a patient, causing millions of positrons to be emitted within the patient. These positrons travel for very short distances, on the order of a few millimeters, and in their travel interact with electrons of similar mass. When positrons and electrons interact, an annihilation event occurs whereby the mass of the positron and electron are annihilated or disintegrated and photons are emitted at substantially 180° with respect to one another. Positrons are positively charged electrons, usually emitted by radionuclides which are unstable because they include an excess of neutrons with respect to a stable state. Positrons lose their kinetic energy in a manner similar to that of electrons. However, when positrons are brought to rest they undergo the phenomenon of annihilation, whereby the positron interacts with an electron, the two particles undergo annhlation, and the masses are converted into energy in form of two photons called the annihilation photons. These two photons travel at about 180° from each other and each carries an energy of appoximately 511 keV. It is through the simultaneous detection of the two annihilation photons that positron-emitting radio-nuclides are of significance in reconstructing a computed tomography image.

The annihilation photons travel the distance required to impinge upon individual detectors positioned in an array about the patient. In the detectors, the energy carried by the annihilation photons is converted to a flash of light, and it is this flash of light which is sensed by photomultipliers located at the ends of the detectors to thereby permit recording of the annihilation which took place in the patient. In the space of a few minutes, hundreds of thousands of such light flashes are generated and electrical signals representing these flashes are processed by a system which may include a specially programmed digital computer so as to form an image of the area under examination.

Annihilation radiation can be uniquely detected by two scintillation detectors connected to a conicidence circuit. In this arrangement, a count is recorded only if both detectors detect the annihilation photons substantially simultaneously. Annihilation events occurring outside a straight line joining the two detectors cannot be recorded, except in a statistically insignificant occurrence, because the annihilation photons are emitted at about 180° from each other. Therefore, the two detectors operated in time coincidence establish a field of view encompassed by the lines joining them.

Numerous positron emission tomography scanners have been described in the prior art. For example, reference is made to U.S. Pat. Nos. 4,057,727 and 4,150,292. The overwhelming majority of prior art positron emission tomography systems incorporate scintillation or imaging detectors, usually of the sodium iodide type, although at least one prior art system employs bismuth germanate crystals. As used herein, the term detector shall describe any detector useful in nuclear medicine imaging techniques. In its simplest form, a positron emission tomography system consists of two detectors facing each other and scanning across the object at distance angles. In order to achieve high efficiency in collecting the radiation, more detectors can be placed around the object. Typically, the design of detector arrays for this purpose is a circle of detectors.

It should be noted that the diagnostic tomographic visualisation of an organ typically requires several tomographic sections. Therefore, tomographs capable of yielding only one section at a time must be provided sequentially with relative movement of the tomograph to achieve each section. This approach is wasteful of radiation, is time consuming, and is often unsuitable for the study of time-dependent dynamic phenomena throughout the organ image. Further, accurate indexing of the apparatus with respect to the patient is difficult. To alleviate this difficulty, prior art positron imaging systems incorporate the ability to provide several sections simultaneously. One system providing simultaneous images is described in the article by Brooks et al. "DESIGN OF A HIGH RESOLUTION POSITRON EMISSION TOMOGRAPH: The Neuro-PET," which appeared in the Journal of Computer Assisted Tomography, volume 4, No. 1, 1980, printed by Raven Press of New York City. The disclosure appearing in that publication is expressly incorporated herein by reference. This Brooks et al system describes an arrangement whereby four circular arrays of bismuth germanate detectors are arranged in four respective planes, each plane being sub-divided into four quadrants. Other PET scanners similarly have four planes of detectors. In all of these prior art systems, however, a problem exists with respect to detecting a cross-slice annihilation event. More particularly, a cross-slice event is defined as a coincidence of gamma ray capture events in two detectors residing in different planes. In the prior art, implementation of cross-slice event data handling is extremely complex and expensive.

SUMMARY OF THE INVENTION

It is the primary object of the present invention to provide a method and apparatus for simplifying data handling of cross-slice annihilation events in positron emission tomography scanners. It is a further object of the present invention is implement cross-slice event data handling in a reliable, effective, and inexpensive manner.

In accordance with the present invention, a positron emission tomography scanner employs a novel data handling system for each pair of planar detector arrays, thereby facilitating extraction of cross-slice data in an unusually simple manner. The invention is described with specific reference to the Brooks et al system (i.e., The Neuro-PET) and adds only a coincidence detector, an OR gate and an output register to the data handling circuitry for each pair of planar detector arrays. The coincidence detector responds to coincident detection of annihilation events in each of the planar detector arrays with which that coincidence detector is associated to actuate an OR gate in the data handling circuitry for each of those arrays. The OR gate may also be actuated by means of other circuitry which detects coincidence in detectors located in any two quadrants of the associated planar array. Enabling of the OR gate in either manner permits processing to proceed in a normal manner whereby the event-detecting detector is identified in each array and the detector identification information is stored in a register for use by a computer to reconstruct an image. When coincident detections are made from two arrays, the information is stored in the additional register rather than in the register associated with the intra-slice coincidence detection.

BRIEF DESCRIPTION OF THE DRAWINGS

The above and still further objects, features and advantages of the present invention will become apparent upon consideration of the following detailed description of one specific embodiment thereof, especially when taken in conjunction with the accompanying drawings, wherein.

DESCRIPTION OF THE PREFERRED EMBODIMENT

Figure 1:
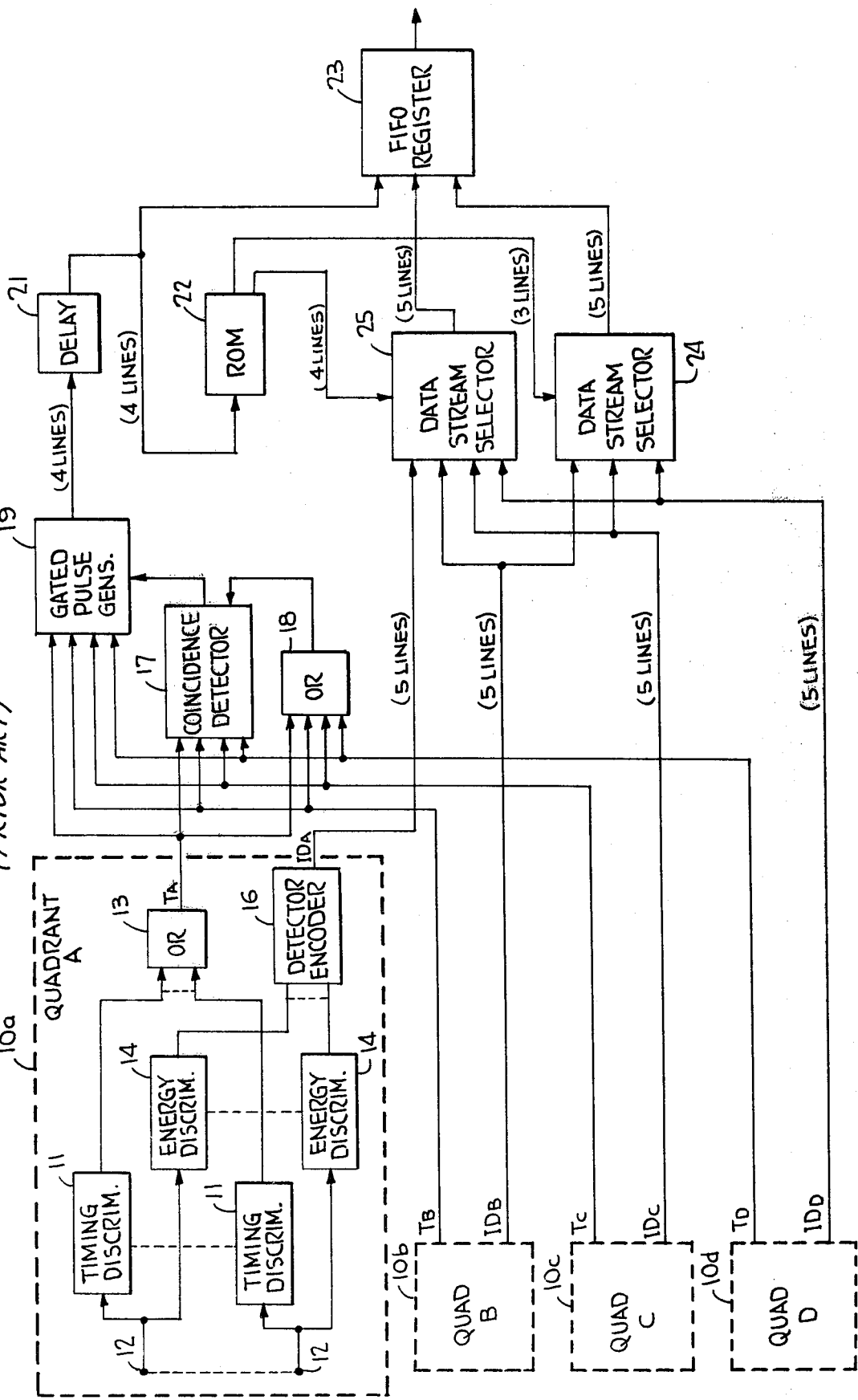
FIG. 1 is a functional block diagram of the data handling system for one planar detector array in the Neuro-PET system described in the above-referenced Brooks et al publication.

FIG. 1 is a functional block diagram which is essentially the same as the diagram appearing in the above-referenced Brooks et al Neuro-PET disclosure as FIG. 6. Certain additions and deletions have been made for purposes of clarity of the present description.

Referring specifically to FIG. 1, four quadrant discriminator circuits 10a, 10b, 10c are illustrated with only circuit 10a being shown in detail, it being understood that circuits 10b, 10c and 10d are identical to circuit 10a. It should also be understood that the circuitry of FIG. 1 relates to a single four-quadrant array and that the Neuro-PET system includes four such arrays and, therefore, four identical circuits of the type illustrated in FIG. 1. Referring to circuit 10a for quadrant A, there are thirty-two input terminals 12 illustrated, one for each detector in quadrant A of the planar array. The scintillation detectors and pre-amplifiers connected to each terminal 12 are not illustrated in order to simplify illustration and understanding of the invention. The signal from each detector is applied to a respective timing discriminator circuit 11 which is simply a voltage discriminator that is set to respond to a very low voltage level corresponding to the first detected photon. Timing discriminator circuit 11 provides an output pulse of 50 nanosecond duration in response to each received pulse above the low discimination voltage level. The output pulse from timing discriminator circuit 11 is delayed for appoximately 35 nanoseconds to permit the following circuitry to ensure that the event is not merely noise. The output pulse from the timing discriminator is applied to a respective input terminal of OR gate 13. OR gate 13 has thirty-two input terminals, one for each timing discriminator circuit 11 in quadrant A. OR gate 13 provides an output pulse $T_A$ when an input pulse is received from any of the timing discriminator circuits 11 in circuit 10a.

Each terminal 12 is also coupled to a respective energy discriminator circuit 14, there being thirty-two such circuits in circuit 10a. Energy discriminator circuit 14 has a considerably higher threshold than timing discriminator 11, which threshold is adjustable in order to permit it to be set high for high count rate studies. Received detector signals above the threshold level result in an output pulse of 100 nanosecond duration, delayed by 500 nanoseconds. The output pulses from the thirty-two energy discriminator circuits 14 in circuit 10a are applied to a detector encoder circuit 16 which provides a parallel binary ouput signal $ID_A$ on five lines. The binary signal $ID_A$ represents the identity of the scintillation detector which has received a signal of sufficient level to trigger its respective energy discriminator circuit 14.

The signals $T_A$ and $ID_A$ have counterpart signals from the other quadrants namely $T_B$ and $ID_B$ from circuit 10b, signals $T_C$ and $ID_C$ from circuit 10c, and signals $T_D$ and $ID_D$ from circuit 10d. The signals $T_A$, $T_B$, $T_C$ and $T_D$ are applied to a four-input coincidence detector 17 and to an OR gate 18. Coincidence detector 17 and OR gate 18 may, for example, be of the type disclosed in U.S. patent application Ser. No. 222,936, filed on Jan. 6, 1981 to the name of Walter S. Friauf and having the title "FOUR-INPUT COINCIDENCE DETECTOR." OR gate 18 is an integral part of that circuit. Coincidence detector 17 provides an output pulse whenever there is time coincidence between any two of its input signals. As described in the aformentioned Friauf patent application, which is expressly incorporated herein by reference, the coincidence detector 17 includes an adjustable coincidence window provided by combinations of two nanosecond gate delays. In practice, considering potential fluctuations of several nanoseconds and drift among the one-hundred-twenty-eight detectors in a planar array, a coincidence window of sixteen nanoseconds or less, with a coincidence resolving time of eight nanoseconds is employed. The coincidence window is adjustable by selecting the number of gate delays so that for high count rate studies it can be set at a minimum value.

The four quadrant timing output signals $T_A$, $T_B$, $T_C$ and $T_D$ are applied to respective gated pulsed generators illustrated for convenience as one common block designated with the reference numeral 19. Time coincidence of any two of the four quadrant timing signals, representing time coincidence of received photons in two corresponding quadrants of the plane detector array, results in two corresponding pulses being simulatenously provided on two of the four output lines from the gated pulse generators 19. These pulses are passed through a delay circuit 21, which delays the pulses for a period on the order of 500 nanoseconds before applying them to the address input terminals of a read only memory 22. The delayed quadrant information is also provided from delay circuit 21 to a first-in first-out register 23.

The four parallel binary information signals $ID_A$, $ID_B$, $ID_C$ and $ID_D$ are passed to a data selector circuit 24, 25 which is addressed by the read only memory 22 in accordance with the quadrant identification initiated by timing signals $T_A$, $T_B$, $T_C$ and $T_D$ via the gated pulse generators 19 and delay circuit 21. Specifically, data stream selector 25 receives the detector identification signals from each of quadrants A, B, C and D and selects the one of those binary signals which corresponds to the address applied thereto from read only memory 22. A binary signal passed by selector 25 thus represents the identification of the photon-receiving detector in one of the quadrants addressed at read only memory 22. Data selector 24 receives only the binary detector identification signals from quadrants B, C and D and selects the one binary signal corresponding to the other addressed quadrant at read only memory 22. Therefore, if detectors in two different quadrants of the array serviced by the circuitry of FIG. 1 received photons, the identity of the detector in one of those quadrants is provided by data stream selector 25 while the identity of the detector in the other of those quadrants is provided by data stream selector 24. Since the detector identity information within each quadrant does not identify the quadrant per se, the quadrant information passed by delay circuit 21 is applied with the selected identification signals from the data stream selectors 24 and 25 to the register 23.

It will be seen that the purpose of delay circuit 21, which as noted above is on the order of 500 nanoseconds, is to permit the energy level discriminators 14 to perform the necessary threshold detection and provide the appropriate output pulse to actuate encoder 16 before selection is made at data stream selectors 24 and 25 by read only memory 22.

The circuitry of FIG. 1 is capable of handling a maximum count rate of onehundred-fifty-thousand counts per second for a single ring array of detectors. Data passed to register 23 is processed in a conventional manner for positron emission tomography systems in order to reconstruct an image of a section of a patient being scanned.

Figure 2:
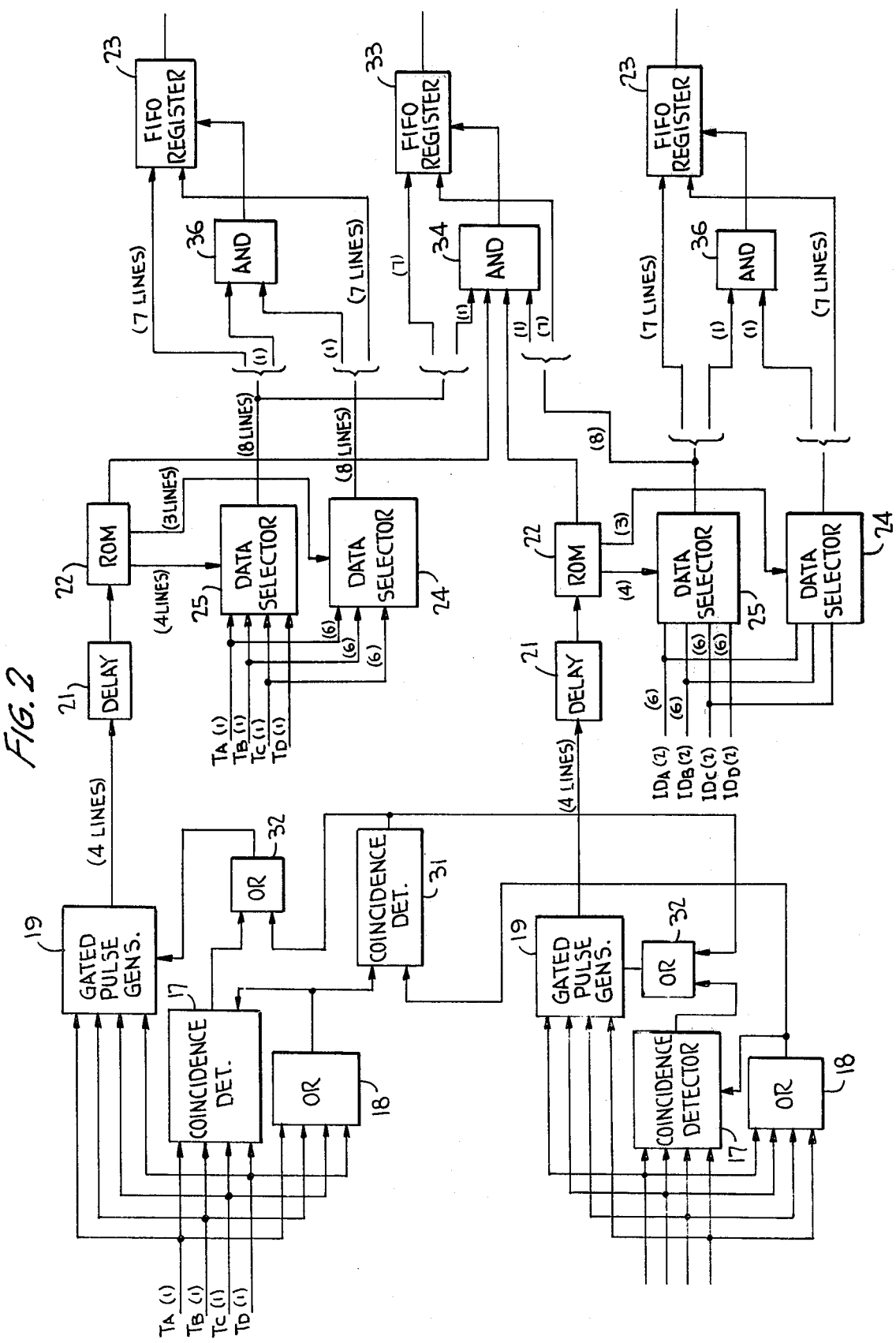
FIG. 2 is a functional block diagram of the portion of the Neuro-PET system modified in accordance with the cross-slice data handling technique of the present invention.

The present invention is illustrated in FIG. 2 which represents a portion of the circuit of FIG. 1 modified by the present invention. Specifically, circuits 10a, 10b, 10c and 10d of FIG. 1 ar not illustrated in FIG. 2; however, the signals $T_A$, $T_B$, $T_C$ and $T_D$ and the signals $ID_A$, $ID_B$, $ID_C$ and $ID_D$ are illustrated in FIG. 2 and are to be understood as being derived from the appropriate quadrant circuits of FIG. 1. In addition, all of these signals are provided with a designation "(1)" or "(2)" signifying that the signals are derived from annihilation events in array (1) or array (2) of the positron emission tomographic system. These two arrays of detectors are planar arrays which are adjacent one another. It will be understood that these two arrays represent any two planar arrays which are adjacent one another. Therefore, while additional circuitry is shown in FIG. 2 for detecting a cross-slice annihilation event between arrays (1) and (2), similar circuitry must be added to detect cross-slice events between arrays (2) and (3) and between arrays (3) and (4). It should be further understood that elements illustrated in FIG. 1 which also appear in FIG. 2 are designated by the same reference numerals for both of the detector arrays.

Referring specifically in FIG. 2, it is noted that a two-input coincidence detector 31 is added, above and beyond the circuitry of FIG. 1, and is common to the circuitry for arrays (1) and (2). Coincidence detector 31 may be, for example, of the type described as a two-input coincidence detector in the above-referenced Friauf patent application. The two-input signals for coincidence detector 31 are derived from the output signals of OR gates 18 for each of arrays (1) and (2). Another OR gate 32 is added for each array and receives an input signal from its associated coincidence detector 17 and from the coincidence detector 31 used in common with the circuitry for the adjacent array. For purposes of simplification, circuitry for only the first and second arrays is illustrated; however, it should be noted that cross-slice event information between arrays (2) and (3) would require that a third input signal be applied to the OR gate in the circuitry of array (2) from a coincidence detector 31 used in common between the circuitry of arrays (2) and (3). OR gate 32 in the circuitry for array (1) receives only two input signals since there is only one array adjacent array (1) for which cross-slice data must be collected. Whereas the gated pulse generators 19 in FIG. 1 are gated by the output signal from coincidence detector 17, the gated pulse generators 19 in FIG. 2 are gated by the output signal from OR gate 32 so that the pulse generators are effectively gated by either the output signal from coincidence detector 17 or the output signal from coincidence detector 31. In other words, if, in array (1), an intra-slice event is detected in two quadrants, coincidence detector 17 will gate gated pulse generators 19 via OR gate 32 so that two timing pulses are passed at gated pulse generators 19 to delay circuit 21. If, on the other hand, coincidence is detected between a detector in array (1) and a detector in array (2), the gated pulse generators in both arrays (1) and (2) are gated by the output from coincidence detector 31 via respective OR gates 32. Under such circumstances only one of the four output lines from the gated pulse generators in each of the arrays passes a pulse to its respective delay circuit 21.

In each array, the output pulse from delay circuitry 21 is once again passed to the read only memory 22. It should be noted that the output lines from delay circuit 21 are not passed to the register 23 in the circuit of FIG. 2; this is because the quadrant information required by the register is provided from the data selectors 24, 25 in the embodiment of FIG. 2. Specifically, it is noted that detector identification signals $ID_A$, $ID_B$, $ID_C$ and $ID_D$ are six-bit signals in the FIG. 2 circuit but are only five-bit signals in the FIG. 1 circuit. The extra bit in the identification signal is an energy verification bit which signifies that the threshold of the energy level discriminator circuit 14 (FIG. 1) has been exceeded. Two bits of hardwired quadrant identification code are added to the five-bit detector identification code and the single energy verification bit to provide an eight-bit output signal from each of the data selectors 24, 25. The two hard-wired bits from the data selectors are selected, along with the detector identification code, by the read only memory output lines which address the respective data selectors. It should be noted that, as in FIG. 1, the quadrant identification bits could be obtained directly from the read only memory 22.

In the case of a cross-slice event, the seven-bits of quadrant and dectector identification information are presented to the first-in-first-out register 33 from each of data selectors 25 in arrays (1) and (2). Register 33 is common to the circuitry for arrays (1) and (2); similar registers are provided to detect cross-slice events as between arrays (2) and (3) and between arrays (3) and (4). The energy verification bit provided at the output of data selectors 25 in each of the two adjacent arrays is applied to a four-input AND gate 34 which serves arrays (1) and (2) in common.

Read only memory 22 is programmed to address data selector 25 when only one of the input lines to that read only memory is pulsed. Receipt of a pulse in only one of its input lines at read only memory 22 designates to that memory that a cross-slice event has occurred and that only data selector 25 should be addressed. Also, when a pulse appears on only one of its input lines, read only memory 22 provides an output pulse to AND gate 34, again signifying that a cross-slice event has occurred. Thus four input signals to AND gate 34 are derived as the two energy verification bits from adjacent arrays and the two cross-slice event indicating bits from the read only memories 22 of the adjacent arrays. If all four inputs to AND gate 34 are present, the binary numbers from data selectors 25 in the adjacent arrays are loaded into register 33 for ultimate use by the computer in reconstructing an image with cross-slice information.

A two-input AND gate 36 is provided as part of the circuitry for each array. AND gate 36 receives the energy verification bit provided at the output of each of the data selectors 24, 25. Under such circumstances, these data selectors have been addressed by read only memory 22, signifying that two of the input lines to that memory have received pulses and that an intra-slice event has occurred. AND gate 36 is enabled by the two energy verification bits and provides an output signal which causes register 23 to load the two seven-bit quadrant and detector identification signals into the register.

An important feature of the invention as described, in relation to FIG. 2, is the extreme economy with which cross-slice data handling is implemented. The addition of the two-input coicidence detector 31 in common to each adjacent pair of arrays, an OR gate 32 in each array, an AND gate 34 in common to each pair of adjacent arrays, and a register 33 in common to each pair of adjacent arrays is all that is required for implementation of this feature. It is noted that AND gates 36 appear to be additional components in FIG. 2 when compared to the circuitry of FIG. 1; however, this relates to a different implementation from that illustrated in FIG. 1 for loading register 23. Importantly, the intermediate data handling for the inter-slice event processing is accomplished with much of the same circuitry used for intra-slice event processing. No additional pulse generators, delay lines, read only memories, or data stream selectors are required.

The present invention has been described as applicable specifically to the Neuro-PET system but is of course applicable to other positron emission tomography systems employing similar types of coincidence detection and data selection techniques.

While we have described and illustrated one specific embodiment of our invention, it will be clear that variations of the details of construction which are specifically illustrated and described may be resorted to without departing from the true spirit and scope of the invention as defined in the appended claims.

We claim:

1. A positron emission tomography scanner of a type wherein at least two planar arrays of photon detectors are each subdivided into sections of sequential detectors, and wherein reception of a photon by a receiving detector results in generation of a timing pulse designating the section in which the receiving detector is located and an identification signal coded to identify that receiving detector, the improvement comprising:

first coincidence detection means for each array for providing a first signal in response to substantially time-coincident generation of two of said timing pulses resulting from reception of photons at two respective receiving detectors designating different sections of one array of said two arrays;

second coincidence detection means in common to said two arrays for providing a second signal in response to substantially time-coincident generation of two of said timing pulses designating sections in said two arrays;

first, second and third register means;

first array processing means responsive to said first signal from one of said arrays for storing the identification signal for the two receiving detectors of said one array in said first register means;

second array means responsive to said first signal from the other array of said two arrays for storing the identification signal for the two receiving detectors of said other array in said second register means; and means responsive to said second signal for storing the identification signal from the two receiving detectors of said two arrays in said third register means.

2. A combination according to claim 1 further comprising:

detector encoder means for each of said sections for providing only one of said identification signals for its section at a time;

wherein said first and second means each includes:

first data selector means for receiving the identification signals from all sections in its array and passing only one of the received identification signals in accordance with a first address signal applied thereto;

second data selector means for receiving the identification signals from all sections in its array and passing only one of the received identification signals in accordance with a second address signal applied thereto;

address means responsive to two substantially time-coincident timing pulses in its array for applying said first and second address signals to said first and second data selector means, respectively, and responsive to receiving only one timing pulse at a time in its array for applying said first address signal to said first data selector means.

3. A combination according to claim 2, further comprising:

a plurality of gated pulse generators, one for each of said sections, responsive to application of a gating signal thereto for passing a respective timing pulse to said address means; and means in each array responsive to receiving either said first or second signal for applying said gating signal to the gated pulse generators for each section in said each array.

4. A combination according to claim 3, further comprising delay means for delaying application of timing pulses to said address means from said plurality of gated pulse generators.

5. The combination according to claim 2, 3 or 4 wherein said address means includes a read only memory.

6. In a positron emission tomography scanner of the type wherein at least two planar arrays of photon detectors are each sub-divided into sections of sequential detectors, and wherein reception of a photon by a receiving detector results in generation of a timing pulse designating the section in which the receiving detector is located and an identification signal coded to identify that receiving detector located in its section, a method for processing both intra-array and inter-array detection events comprising the steps of:

for each array, providing a first signal in response to substantially time-coincident generation of two of said timing pulses resulting from reception of two photons at two respective detectors and designating different sections of one array of said two arrays;

providing a second signal in common to said two arrays in response to substantially time-coincident generation of two of said timing pulses designating sections in said two arrays;

in response to said first signal from one of said arrays, storing the identification signal for the two receiving detectors in said one array in a first register;

in response to said first signal from the other array of said two arrays, storing the identification signal for the two receiving detectors of said other array in a second register; and in response to said second signal, storing the identification signals from the two receiving detectors of said two arrays in a third register.

7. The method according to claim 6, further comprising the steps of:

for each of said sections, providing only one of said identification signals for each section at a time;

for each of said first and second arrays:

grouping at a first data selector the identification signals from all sections in its array and passing only one of the received identification signals in accordance with a first address signal applied to the first data selector;

grouping at a second data selector the identification signals from all sections in an array and passing only one of the received identification signals in accordance with a second address signal applied to the second data selector;

in response to two-substantially time-coincident timing pulses in its array, applying the first and second address signals to the first and second data selector means;

in response to receiving only one timing pulse in its array, applying said first address signal only to said first data selector.

* * * * *